(12) United States Patent
Kawai et al.

(10) Patent No.: US 8,278,508 B2
(45) Date of Patent: Oct. 2, 2012

(54) HON-SHIMEJI MUSHROOM-FUNGAL BED CULTURE

(75) Inventors: Takashi Kawai, Shiga (JP); Katsuhiko Kusakabe, Shiga (JP); Akihiko Kita, Shiga (JP); Ikunoshin Kato, Shiga (JP)

(73) Assignee: Takara Bio Inc., Shiga (JP)

( * ) Notice: Subject to any disclaimer, the term of this patent is extended or adjusted under 35 U.S.C. 154(b) by 882 days.

(21) Appl. No.: 12/272,758

(22) Filed: Nov. 17, 2008

(65) Prior Publication Data
US 2009/0148926 A1  Jun. 11, 2009

(30) Foreign Application Priority Data
Nov. 15, 2007  (JP) ................. 2007-296895

(51) Int. Cl.
*A01H 15/00* (2006.01)
*A01N 63/00* (2006.01)
*A01N 63/04* (2006.01)
*C12N 1/14* (2006.01)
*C12N 1/16* (2006.01)

(52) U.S. Cl. ............ 800/297; 424/93.5; 435/254.1
(58) Field of Classification Search ............ 424/93.5; 435/254.1; 800/297
See application file for complete search history.

(56) References Cited

FOREIGN PATENT DOCUMENTS

| JP | 06-153695 | A | 6/1994 |
|---|---|---|---|
| JP | 07-115844 | A | 5/1995 |
| JP | 2000-106752 | A | 4/2000 |
| JP | 2002-247917 | A | 9/2002 |
| JP | 2005-027585 | A | 2/2005 |
| JP | 2007-054044 | A | 3/2007 |

OTHER PUBLICATIONS

Kawato, Tetsuya, 2007, JP 2007054044, English translation, p. 1-6.*
A. Ohta, "Culture conditions for commercial production of *Lyophyllum shimeji*", Journal of the Mycological Society of Japan, 1998, p. 13-20, vol. 39.
H. Yoshida, et al., "A trial cultivation of *Lyophyllum shimeji* on solid media", Journal of the Mycological Society of Japan, 1994, p. 192-195, vol. 35.

* cited by examiner

*Primary Examiner* — Shin-Lin Chen
(74) *Attorney, Agent, or Firm* — Browdy and Neimark, PLLC

(57) ABSTRACT

The present invention provides a fungal bed culture of a hon-shimeji mushroom inoculated with a liquid seed culture wherein the surface of a culture medium for cultivation has a liquid seed culture inoculated portion and a liquid seed culture non-inoculated portion as well as provides a fungal bed cultivation method of a hon-shimeji mushroom which generates a fruit body from the fungal bed culture. According to the present invention, the formation rate of budlet in the fungal bed cultivation of a hon-shimeji mushroom is improved, thereby enabling stable production of a hon-shimeji mushroom in large scale commercial cultivation.

3 Claims, 1 Drawing Sheet

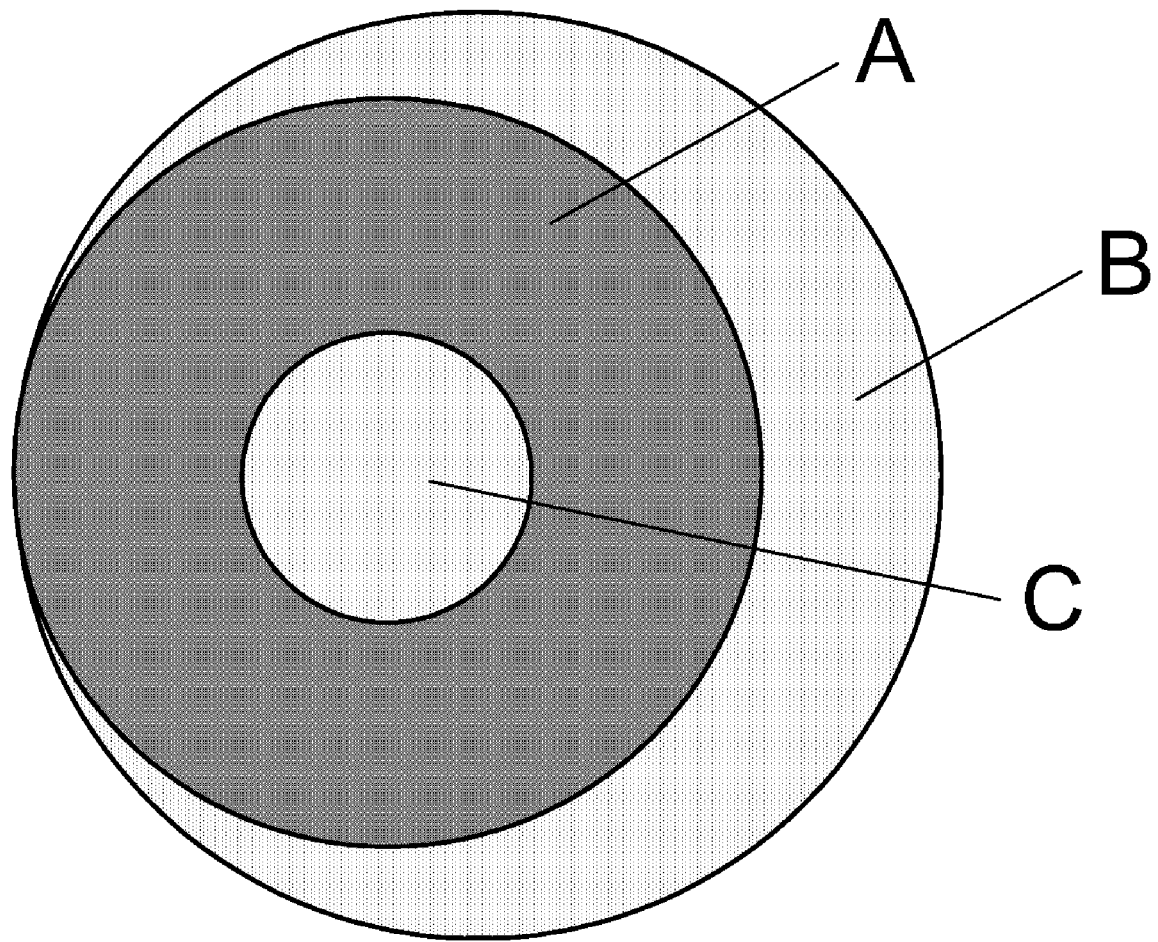

HON-SHIMEJI MUSHROOM-FUNGAL BED CULTURE

TECHNICAL FIELD

The present invention relates to a fungal bed culture to be used for fungal bed cultivation of a hon-shimeji mushroom (*Lyophyllum shimeji*).

BACKGROUND ART

A hon-shimeji mushroom is a mushroom, which generates on the ground surface in a forest of *quercus serrata* grove or a mixed forest of *quercus serrata* and red pine around in the middle of October. As people say "a hon-shimeji mushroom is excellent in taste, while a matsutake mushroom is excellent in flavor", a hon-shimeji mushroom as well as a matsutake mushroom are recognized as the highest grade edible mushrooms in Japan. Recently, for edible mushrooms including an enokitake mushroom (*Flammulina velutipes*), a hiratake mushroom (*Pleurotus ostreatus*), a nameko mushroom (*Pholiota nameko*), a bunashimeji mushroom (*Hypsizigus marmoreus, Lyophyllum ulmarium*), a maitake mushroom (*Grifola frondosa*) and the like, a fungal bed cultivation method has been established, wherein a mushroom is artificially cultivated by using a culture medium containing mixed nutrient sources of sawdust, rice bran, wheat bran and the like. Thus, these mushrooms can be harvested stably in any season throughout the year. Although it has also been desired to establish an artificial cultivation method of a hon-shimeji mushroom because of its excellent taste, an artificial fungal bed cultivation thereof has been considered to be difficult because a hon-shimeji mushroom is a mycorrhizal fungus, while the above mentioned enokitake mushroom and the like are wood-rotting fungi.

Ohta of Shiga Prefectural Forest Research Center succeeded in a fungal bed cultivation of a hon-shimeji mushroom for the first time. Patent Document 1 discloses a fungal bed cultivation method of a hon-shimeji mushroom using wheat and the like, and non-Patent Document 1 discloses an experiment for generating fruit body of a hon-shimeji mushroom using a culture medium containing wheat and the like.

In addition, Patent Document 2 discloses a method for incubating the mycelia of a mycorrhizal fungus using a culture medium in which peat moss is used as a base material and starch and the like are added thereto and, in non-Patent Document 2, the inventors of the above patent document report an experiment for generating fruit body of a hon-shimeji mushroom using a culture medium in which peat moss is used as a base material, and starch and the like are added thereto.

However, the method described in Patent Document 1 requires much cost for a culture medium because wheat, and the like used in the culture medium are expensive. Further, the method described in Patent Document 2 does not reach a commercial production level due to a low yield of a fruit body.

Recently, various cultivation methods of a hon-shimeji mushroom have been disclosed for the commercial production of a hon-shimeji mushroom. Patent Document 3 discloses a culture medium for fungal bed cultivation of a hon-shimeji mushroom which comprises Panicoideae plant, and a method for cultivating a hon-shimeji mushroom using the culture medium. Further, Patent Document 4 discloses a fungal bed cultivation method of a hon-shimeji mushroom which comprises preparing a mixed culture medium containing at least corn powder and sawdust of broad leaf tree, inoculating the mycelia of a hon-shimeji mushroom on the mixed culture medium in a moisturized wet state, and incubating the culture medium at a temperature of 30° C. or lower to generate a fruit body.

Patent Document 5 discloses a fungal bed cultivation method of a hon-shimeji mushroom which comprises adding crushed oyster shell to a culture medium on which the mycelia of a hon-shimeji mushroom have been inoculated so that a fruit body can generate by incubating, them in a moisturized wet state, and adjusting pH of the culture medium to a range below 7.

Patent Document 6 discloses a fungal bed cultivation method of a hon-shimeji mushroom which comprises using a mixed culture medium prepared by adding small amounts of wheat and/or rice to a culture medium containing corn and sawdust and mixing them, inoculating the mycelia of hon-shimeji mushroom on the culture medium in a moisturized wet state, and incubating it to generate a fruit body.

The Example of Patent Document 1 investigates whether or not a hon-shimeji mushroom strain forms primordia of a fruit body when the mycelia are incubated at 23° C. for 70 days, followed by lowering the temperature to 15° C. And, a formation ratio of a fruit body has been increased by covering the surface of the culture medium with peat. Further, in non-Patent Document 1, the surface of a culture medium is covered with peat with a thickness of 1 cm, when the mycelia of a hon-shimeji mushroom are extended in an incubation step at 22° C. Then, the culture medium is further incubated for additional two weeks and, after completion of incubation, the culture medium is transferred to a generation room at 15° C. to generate a fruit body.

In non-Patent Document 2, formation of primordia of a fruit body is recognized on the 13th to 15th day after incubation of a hon-shimeji mushroom strain by inoculating the mycelia of the strain on a culture medium, incubating and maturing it at 23° C., and then carrying out a generation operation in a generation room at 16° C.

Patent Document 3 discloses a bottle cultivation method which comprises steps of preparation of a culture medium, filling of a bottle, sterilization of the culture medium, inoculation, incubation (culture), sprouting, growth (cultivation), and harvesting, wherein primordia of a fruit body is formed in the step of sprouting after incubation. Further, in Example thereof, the sprouting is carried out with a cover of Akadama soil.

In Example of Patent Document 4, generation of a fruit body of a hon-shimeji mushroom strain is promoted by incubating the strain at 23° C. for 60 days, incubating the mycelia for additional 7 days with covering the surface of a culture medium with Kanuma soil, transferring the culture medium to a generation room at 15° C.

In Example of Patent Document 5, the mycelia of hon-shimeji mushroom strain is incubated at 23° C. for 70 days, the culture medium is transferred to a generation room at 15° C., and the cap is removed when a small fruit body is appeared, then the fruit bodies are harvested when pilei have grown to open.

In Example of Patent Document 6, the mycelia of hon-shimeji mushroom strain is incubated at 23° C. for 55 days, further incubated for additional 10 days with covering the surface of the culture medium with Kanuma soil, and the culture medium is transferred to a generation room at 15° C. to promote generation of a fruit body.

Patent Document 1: JP 7-115844 A
Patent Document 2: JP 6-153695 A
Patent Document 3: JP 2000-106752 A
Patent Document 4: JP 2002-247917 A Patent Document 5: JP 2005-27585 A
Patent Document 6: JP 2007-54044 A
Non-patent Document 1: "Nihon-Kingakkai Kaihou" (Journal of the Mycological Society of Japan), volume 39, pages 13-20, 1998
Non-patent Document 2: "Nihon-Kingakkai Kaihou" (Journal of the Mycological Society of Japan), volume 35, pages 192-195, 1994

DISCLOSURE OF THE INVENTION

Problem to be Solved by the Invention

The present inventors have already started commercial cultivation of a hon-shimeji mushroom based on the technique described in Patent Document 3. However, because stabilization of the production is required for large scale commercial cultivation, it has been desired to further develop additional techniques.

Thus, in view of the above situation, the object of the present invention is to provide a fungal bed culture which permits stable production of a hon-shimeji mushroom by cultivation in a commercially large scale, and a fungal bed cultivation method of a hon-shimeji mushroom using the artificial culture.

Means for Solving the Problem

The present inventors have carried out a cultivation study with respect to each of various factors which affect fungal bed cultivation of a hon-shimeji mushroom to intensively investigate the effect thereof on large-scaled commercial cultivation. In cultivation of a mushroom using a liquid seed culture, when the liquid seed culture is inoculated on the surface (upper part) of a culture medium for cultivation, the liquid seed culture is usually inoculated on the entire surface so that sprouts (budlet) are formed on the entire surface of the culture medium. However, as a result of the present inventors' intensively study of an inoculation method suitable for commercial cultivation, the present inventors have surprisingly found that a formation rate of sprouts (budlet) increases if a non-inoculated portion is provided upon inoculating a liquid seed culture on the surface of a culture medium for cultivation as compared with a conventional method. Thus, the present invention has been completed.

In brief, the first invention of the present invention relates to a fungal bed culture of a hon-shimeji mushroom inoculated with a liquid seed culture characterized in that the surface of a culture medium for cultivation has a liquid seed culture inoculated portion and a liquid seed culture non-inoculated portion.

As the aspects of the first invention of the present invention, a fungal bed culture for bottle cultivation is exemplified. In the preferred aspects, the liquid seed culture inoculated portion has a substantially circle, oval, circular doughnut-like or oval doughnut-like shape plan view. The more preferred aspects relates to a fungal bed culture of a hon-shimeji mushroom, wherein the liquid seed culture is inoculated in an amount of 0.05 to 5 mL/cm$^2$ at the liquid seed culture inoculated portion. A ratio of an area of the liquid seed culture inoculated portion to that of the liquid seed culture non-inoculated portion in the surface of the culture medium is not particularly limited, but is preferably from 1:15 to 5:1.

Further, the second invention of the present invention is an artificial cultivation method of a hon-shimeji mushroom characterized by generating a fruit body from the fungal bed culture of a hon-shimeji mushroom according to the first invention of the present invention.

According to the present invention, there is also provided a method for inoculation of a liquid seed culture of a hon-shimeji mushroom for fungal bed cultivation of a hon-shimeji mushroom characterized in that a liquid seed culture inoculated portion and a liquid seed culture non-inoculated portion are formed on the surface of a culture medium for cultivation. The inoculation method is not particularly limited, but inoculation to a culture medium for cultivation packed in a cultivation bottle while applying pressure is preferred. Further, the shape of the liquid seed culture inoculated portion is not particularly limited, but it is preferred that the liquid seed culture inoculated portion has a substantially circle, oval, circular doughnut-like or oval doughnut-like shape plan view. It is also preferred that the liquid seed culture is inoculated at a concentration of 0.05 to 5 mL/cm$^2$ at the liquid seed culture inoculated portion, although not particularly limited. A ratio of an area of the liquid seed culture inoculated portion to that of the liquid seed culture non-inoculated portion in the surface of a culture medium is not particularly limited, but is preferably from 1:15 to 5:1.

Effect of the Invention

According to the present invention, there are provided a fungal bed culture of a hon-shimeji mushroom, which permits a stable production of a hon-shimeji mushroom in a commercially large scale as well as a fungal bed cultivation method of a hon-shimeji mushroom using the culture.

BEST MODE FOR CARRYING OUT THE INVENTION

Hereinafter, the present invention will be explained in detail.

The hon-shimeji mushroom as used herein is referred to a mushroom taxonomically classified into *Lyophyllum shimeji*

The hon-shimeji strain to be used in the present invention is not particularly limited and can be selected any strain as long as it can be artificially cultivated. Examples thereof include known hon-shimeji mushroom strains such as *Lyophyllum shimeji* La 01-27 (FERM BP-10960), *Lyophyllum shimeji* La 01-20 (FERM BP-10959), *Lyophyllum shimeji* La 01-37 (FERM P-17456), *Lyophyllum shimeji* La 01-45 (FERM P-17457), *Lyophyllum shimeji* La 01-46 (FERM P-17458), and variants thereof suitable for cultivation.

The "surface of culture medium" as used herein refers to the surface portion of an upper part of a culture medium for cultivation on fungal bed and is formed from a liquid seed culture inoculated portion at which a liquid seed culture is inoculated and a liquid seed culture non-inoculated portion at which a liquid seed culture is not inoculated.

The cultivation method of a hon-shimeji mushroom of the present invention is not particularly limited as long as the cultivation is characterized by using a fungal bed culture of a hon-shimeji mushroom inoculated with a liquid seed culture characterized in that the surface of a culture medium for cultivation has a liquid seed culture inoculated portion and a liquid seed culture non-inoculated portion. Fungal bed cultivation methods such as bottle cultivation, bag cultivation, box cultivation and the like can be applied to the cultivation method of a hon-shimeji mushroom of the present invention. By fungal bed cultivation using the said culture, a formation rate of sprouts (budlet) of a hon-shimeji mushroom is unexpectedly improved and the production of a hon-shimeji mushroom is extremely stabilized in large-scaled commercial cultivation.

Hereinafter, the fungal bed cultivation method of a hon-shimeji mushroom of the present invention will be explained by using bottle cultivation as an example. This method comprises the steps of preparation of a culture medium, filling in bottle(s), sterilization, inoculation, incubation, formation of primordia, sprouting (formation and growth of budlet), selection of sprouts (budlet) if necessary, growth from budlet to mature fruit body, harvest of mature fruit body, and the like. These steps will be specifically illustrated hereinafter, but the present invention is not limited thereto.

The "preparation of a culture medium" refers to a step comprising measuring various base materials used for fungal bed cultivation, stirring the base materials and adding water to adjust the water content of the culture medium which is suitable for fungal bed cultivation of a hon-shimeji mushroom. The culture medium for the fungal bed cultivation of a hon-shimeji mushroom to be used in the present invention is not particularly limited as long as the culture medium can be utilized for cultivation. A combination of corn and sawdust is preferred. As sawdust, both sawdust of broadleaf tree origin and needle-leaved tree origin can be used, and sawdust of needle-leaved tree origin, for example, sawdust of Japanese cedar origin (Japanese cedar sawdust) is preferred. As used herein, corn is not particularly limited as long as it contains corn seeds, and examples thereof include fresh corn seeds, dry corn seeds, ground corn, rolled corn, and heat rolled corn.

A mixing ratio of corn and sawdust of needle-leaved tree origin will be explained by using a case of heat rolled corn and sawdust of Japanese cedar origin (Japanese cedar sawdust) as an example. The mixing ratio of corn and sawdust of needle-leaved tree origin is not particularly limited as long as a hon-shimeji mushroom can be cultivated. From a viewpoint of obtaining a high yield, the amount of heat rolled corn is at least 40% or more, preferably 50% or more, more preferably 60% or more in a culture medium for fungal bed cultivation in terms of a dry weight ratio. When the amount is less than 40%, a yield of a hon-shimeji mushroom is significantly decreased and is not preferred. Further, because heat rolled corn has low water absorbability, when the amount of heat rolled corn in a culture medium for fungal bed cultivation becomes too much, water holding capability of a culture medium for fungal bed cultivation is decreased to cause retention of water at the bottom of a cultivation bottle, which results in poor extension of the mycelia. Therefore, the amount of heat rolled corn is at most 80% or less, preferably 75% or less, more preferably 70% or less in a culture medium for fungal bed cultivation in terms of a dry weight ratio.

Further, the water content in a culture medium for fungal bed cultivation will be also explained by using a case of heat rolled corn and Japanese cedar sawdust as an example. The water content in a culture medium for fungal bed cultivation is preferably adjusted so as to avoid water retention at the bottom of a cultivation bottle according to one skilled in the art. For example, the water content is, but is not limited to, 68% by weight or less, preferably 66% by weight or less. However, when the water content exceeds 64% by weight, sometimes, voids of a culture medium are decreased to cause poor extension of the mycelia, which results in a low yield and low quality of fruit body. Therefore, the water content is preferably adjusted to 64% by weight or less. However, when the water content becomes too low, poor extension of the mycelia, deformed fruit body and poor growth are caused due to drying and the like of a culture medium. Thus, the water content is preferably adjusted to 50% by weight or more, more preferably 55% by weight or more. The water content is appropriately selected by observing the state of a culture medium whose water content has been adjusted.

The step of "filling in bottle(s)" refers to a step of filling a culture medium for fungal bed cultivation in bottles. Specifically, this step refers to a step of filling a heat-resistant wide-mouthed cultivation bottle of usually 400-2300 mL volume with a prepared culture medium for fungal bed cultivation while applying pressure, for example, when using a 1100 mL bottle, at 550-900 g, preferably 650-850 g, more preferably 650-750 g, followed by making one or more holes of about 1-3 cm diameter on thus filled culture medium for fungal bed cultivation under pressure, and stoppering the bottle with a cap. A hon-shimeji mushroom can be cultivated more preferably by making a hole of 1.5 cm diameter at the center portion of the surface of a culture medium and 4 holes of 1 cm diameter around the hole.

The "sterilization" is not particularly limited as long as it is a step for killing all microorganisms in a culture medium. Usually, in the case using steam, sterilization is carried out at 98-100° C. for 4-12 hours under normal pressure, or at 101-125° C., preferably at 118° C. for 30-90 minutes under high pressure. Herein, thus prepared culture medium is sometimes referred to as a culture medium for cultivation.

The "inoculation" is a step of inoculating a seed culture on a culture medium which has been allowed to stand to cool after sterilization. A liquid seed culture obtained by culturing the mycelia of a hon-shimeji mushroom in a liquid culture medium is used in the present invention.

The liquid culture medium to be used for culturing the liquid seed culture is not particularly limited, but usually, examples thereof include PGY liquid culture medium which is mainly composed of glucose, peptone and yeast extract with addition of $KH_2PO_4$, $MgSO_4/7H_2O$, etc., ½ PGY liquid culture medium, GY culture medium mainly composed of glucose and yeast extract, and ½ GY liquid culture medium. A culture obtained by inoculating hon-shimeji mushroom mycelia in such a liquid culture medium and incubating, for example, at 25° C. for 10-15 days can be used as the liquid seed culture. The incubation of the liquid seed culture can be carried out by using a flask, a jar-fermentor, etc. For carrying out incubation of the liquid seed culture for large scale cultivation, a jar-fermentor is preferred in view of reduction of the incubation period owing to a larger volume. The concentration of the mycelia in the liquid seed culture to be used for inoculation to a culture medium for cultivation is, but not limited to, for example, 0.1 to 10 g/L, preferably 1 to 7 g/L, particularly 2 to 5 g/L in terms of a concentration of dry the mycelia.

The liquid seed culture is inoculated so that a liquid seed culture inoculated portion and a liquid seed culture non-inoculated portion are formed, for example, about 5 to 30 mL is aseptically inoculated per one 1100 mL wide mouthed cultivation bottle. As used herein, the liquid seed culture inoculated portion means a region inoculated with the liquid seed culture, in other words, a region on the surface of a culture medium directly inoculated with the liquid seed culture. As used herein, the liquid seed culture non-inoculated portion means a region other than that inoculated with the liquid seed culture, in other words, the region on the surface of a culture medium not inoculated with the liquid seed culture. There is no particular limit to the shape of the liquid seed culture inoculated portion as long as the liquid seed culture inoculated portion and the liquid seed culture non-inoculated portion are formed on the surface of a culture medium for cultivation. The shape of the liquid seed culture inoculated portion is, for example, a substantially circular, oval or polygonal shape having an area of smaller than that of the surface of a culture medium for cultivation. The shape of the liquid seed culture inoculated portion has preferably a circular or oval shape plan view, more preferably a circular doughnut-like shape plan view having a circular or oval shape center portion of the liquid seed culture non-inoculated portion. The center axis of the liquid seed culture inoculated portion can coincide with that of the bottle mouth or can deviate from the central axis of the bottle mouth. The liquid seed culture inoculated portion can contact with the wall of the bottle. The ratio of the area of the liquid seed culture inoculated portion and the liquid seed culture non-inoculated portion at the surface of a culture medium is selected so that the sprouting formation rate becomes higher as compared with conventional seed culture inoculation. There is no particular limit of the ratio of the area of the liquid seed culture inoculated portion and the liquid seed culture non-inoculated portion and it is preferably 15:1 to 5:1, more preferably 1:5 to 4:1 and yet more preferably 1:3 to 3:1.

There is no particular limit of the amount of the liquid seed culture to be used for inoculation on the culture medium for cultivation, but it is preferably 0.05 to 5.0 mL/cm$^2$, more preferably 0.1 to 1.0 mL/cm$^2$, and yet more preferably 0.25 to 0.75 mL/cm$^2$ of the liquid seed culture inoculating portion.

There is no particular limit of the amount of the mycelia to be used for inoculation on the culture medium for cultivation, but it is preferably 0.2 to 10 mg/cm$^2$, more preferably 0.5 to 6 mg/cm$^2$, and yet more preferably 1 to 3 mg/cm$^2$ of the liquid seed culture inoculating portion in terms of a dry weight.

There is no particular limit of the inoculation method of the liquid seed culture as long as the liquid seed culture inoculated portion and the liquid seed culture non-inoculated portion are suitably formed and can be carried out by using a known liquid seed culture inoculating apparatus. As used herein, the culture after the inoculation step is referred to as the "culture" of the present invention.

The "incubation" refers to a step of incubating the culture medium inoculated with a seed culture, and the mycelia are grown, extended and then matured. Usually, a culture medium for fungal bed cultivation on which a seed culture has been inoculated is incubated at a temperature of 20 to 25° C. and humidity of 50 to 80% to extend the mycelia, followed by further maturing. The conditions of the incubation step can be suitably selected based on the volume of the culture medium. The incubation step is usually carried out for 80 to 120 days, and preferably about 100 days when a 1,100 mL bottle is used. The incubation step can be controlled by dividing the step into the incubation first term step and the incubation latter term step, and by somewhat lowering the temperature in the incubation latter term step where the mycelia are actively extended. The incubation first term step is terminated within 75 to 85 days, while the incubation latter term step is terminated within 25 to 35 days.

The "formation of primordia" as used herein refers to the step of forming the primordia of fruit body of hon-shimeji mushrooms. After completion of the incubation step, the culture is transferred into an environment of 19 to 22° C., preferably about 20° C., humidity 60 to 80%, illumination 1,000 lux or less. The cap of each bottle is removed to form the primordia of fruit body. The formation of the primordia step requires 10 to 20 days. The primordia of fruit body can also be formed on the surface of a culture medium, for example, by illuminating for a total of 20 lux-hours or more in the above incubation latter term step.

The "sprouting" is a step of forming sprouts (budlet: a state where grayish white mushroom pilei are formed at tip portions of the primordia differentiated from the primordia of fruit body) from primordia of fruit body and/or enhancing the growth of the sprouts (budlet). The sprouting step is usually carried out at from 10 to 20° C., preferably about 15° C., for 5 to 15 days, at humidity of 80% or more and under the illumination of 1,000 lux or less.

Because bedewing can occur due to humidification during sprouting, for the purpose of preventing the surface of fungal bed from wetting, the surface can be covered with a perforated plastic sheet or a corrugated panel. Alternatively, cultivation bottles can be reversed and incubated. In order to promote growth of budlet, the surface of the fungal bed can be optionally covered with suitable soil.

The "growth from budlet to matured fruit body" is a step of carrying out for 5 to 15 days under the conditions approximately similar to those in the sprouting step except for illuminating the culture medium with illumination of 2,000 lux or less. Because of little effect of wetness bedewing during the step of growth from budlet to mature fruit body, the culture medium is preferably incubated without covering sprouts with a perforated plastic sheet or a corrugated panel.

As used herein, high humidity conditions in which humidity exceeds 100% refer to humidification to more than the saturated aqueous vapor level so that water is present as a mist. In order to quantify such high humidity conditions, the measurement is carried out by using an apparatus from Saginomiya Seisakusho, Inc. (trade name: HUMID EYE 100). This apparatus utilizes a method in which the moisture in the air is reduced by heating and, after a detection operation using a humidity sensor, the reduction owing to heating is corrected. Then, the value shown by this apparatus is equal to relative humidity when it is 100% or less. When this exceeds 100%, the value shown is that obtained by converting the moisture contained in the air into water vapor and expressing as the ratio thereof to the saturated water vapor level. Humidification can be carried out using a humidifier such as an ultrasonic humidifier, a vaporizing humidifier or an atomizing humidifier.

In the step of growth from budlet to mature fruit body, after the sprouting step described above, the step is carried out by removing sprouts (budlet) other than the sprouts at the center of the surface of a culture medium, in other words, the sprouts on the outer edge (wall side of a bottle) of the surface of a culture medium to stably obtain an established strain (multi-sprouting) of mature fruit body at the center part of the bottle. When removing sprouts other than the sprouts at the center part of the surface of a culture medium, mechanical removal can be carried out along the wall part of the bottle. When growing continues after these treatments, the sprouts can be efficiently grown into an established strain of mature fruit body.

The step of sprout selection as used herein is the step of selecting several sprouts which are expected to grow into fruit body from the sprouts growing on the surface of a culture medium in the sprouting step or an initial stage (up to the fifth day) of the step of growth from budlet to mature fruit body described above. By further carrying out the sprout selection step, single-sprouting large fruit body of hon-shimeji mushrooms with high commercial value can be obtained. The sprout selection step can be carried out mechanically by picking the sprouts on the outer edge (wall part of bottle) along the outer edge of the surface of a culture medium. As required, sprouts forming at the center portion of the surface of a culture medium can also be mechanically picked. After these treatments, budlet other than fruit body (budlet) suitable for growth can be further picked to grow the selected residual budlet, thereby allowing the efficient growth of large well-shaped hon-shimeji mushroom fruit body.

Furthermore, the step of isolation and transplantation of cuttings as used herein is a step in which budlet obtained in the sprouting step described above is individually isolated and transplanted as cuttings to any appropriate portion of a culture medium for growing fruit body. By further carrying out the isolation and transplantation step of cuttings, large independently single-sprouting fruit body of hon-shimeji mushrooms with high commercial value can be produced. The culture medium for transplantation of cuttings may be any culture medium used for isolating the cuttings (the culture medium after isolation of the cuttings) or may be the mycelia extending separately prepared culture medium, for example a culture medium used in the cultivation step or a culture medium used in the sprouting step.

According to the above-mentioned steps, matured fruit body can be obtained and the fruit body are then harvested. Thus, all steps of cultivation are completed. Although the present invention has been explained by means of a bottle cultivation method, the present invention can be applied to fungal bed cultivation of mushrooms, and not limited to the above mentioned bottle cultivation.

The present invention provides a fungal bed culture of a hon-shimeji mushroom which improves a sprout (budlet) formation rate and a fungal cultivation method using the said culture. That is, by forming a liquid seed culture inoculated portion and a liquid seed culture non-inoculated portion on the surface of a culture medium, formation of sprouts (budlet) proceeds unexpectedly also from the liquid seed culture non-inoculated portion. Sprout formation occurs on the entire surface of a culture medium and shows a higher rate of sprout formation as compared with the case where the entire surface is inoculated with a seed culture. According to the present invention, a formation rate of budlet is significantly stabilized and improved, thereby making it possible to stably produce a hon-shimeji mushroom in the commercial cultivation thereof. Further, by utilizing that the fact that the number of sprouts increases towards the center of the surface of a culture medium, it is possible to produce an establish strain (multi-sprouting) of a hon-shimeji mushroom. Furthermore, when producing large hon-shimeji mushrooms by combining a sprout picking step, it is possible to constantly remain sprouts at about the center part of the surface of a culture medium where is the most suitable portion for forming fruit body by producing a number of sprouts on the surface of a culture medium according to the present invention, in particular, at the center portion of the surface of a culture medium. Therefore, growth and selection of excellent sprouts at a portion on the surface of a culture medium suitable for growth of large hon-shimeji mushrooms become extremely easy. Furthermore, by combining of the step of transplantation of cuttings for producing large hon-shimeji mushrooms, it is possible to stably obtain a large number of excellent cuttings, thereby improving a yield and allowing stable cultivation of hon-shimeji fruit body.

EXAMPLES

Hereinafter, the present invention will be described in more detail with reference to the following Examples, but the present invention is not limited to only the scope of the Examples.

Example 1

The mycelia of *Lyophyllum shimeji* La 01-27 strain (FERM P-17455) were inoculated to 100 ml of a PGY liquid culture medium (composition: glucose 2.0% (w/v), peptone 0.2% (w/v), yeast extract 0.2% (w/v), $KH_2PO_4$ 0.05% (w/v) and $MgSO_4 \cdot 7H_2O$ 0.05% (w/v)), and the mycelia were incubated at 25° C. for 7 days with shaking (100 rpm). After 2 ml of the resulting culture was subcultured in the same culture medium, the mycelia was further incubated for 7 days with shaking (100 rpm). Then, the entire culture was inoculated to a jar fermentor of 200 L in volume (manufactured by Komatsukawa Seisakusyo) containing 160 L of the same culture medium, and the culture was incubated for 6 days with stirring (stirring rate: 100 rpm, ventilation volume 25 L/minute) to prepare a liquid seed culture. On the other hand, rolled corn (manufactured by Iisaka Seibaku) and Japanese cedar sawdust as sawdust of needle-leaved tree origin (manufactured by Tomoe Bussan Co., Ltd.) were mixed at a dry weight ratio of 2:1 (rolled corn:needle-leaved tree sawdust), and water was added thereto so that the final water content in the culture medium became 62% by weight. The mixture was thoroughly mixed with stirring, and the resulting mixture was filled in wide-mouthed cultivation bottles (each 1100 ml) made of polypropylene (about 5,000 bottles per lot) with applying pressure so that the total weight of each bottle with a cap became 800 g. On the center portion of the surface of the filled culture medium of each bottle, a hole of 2.0 cm diameter and 10 cm in depth was made, and 4 holes each having 1 cm diameter and 10 cm in depth were evenly made on the circumference of a circle of 4 cm diameter whose center was the center of the surface of the filled culture medium. Then, the cultivation bottle was stoppered with a cap. The culture medium was autoclaved at 118° C. for 30 minutes and allowed to stand to cool to 20° C. to prepare a culture medium for fungal bed cultivation (solid culture medium). About 25 ml of the above-mentioned liquid seed culture was inoculated to the solid culture so that the inoculated portion deviated from the center axis of the bottle to form a doughnut-like shape as shown in FIG. 1, and the mycelia were incubated at the temperature of 21° C. and at the humidity of from 70 to 75% for 80 days to entirely extend the mycelia throughout the culture medium. The temperature was dropped by 0.5° C. and the incubation of the mycelia was continued for additional 30 days under the illumination of a total of 20 lux or more. Primordia of fruit body were formed by incubation for total 110 days. FIG. 1 is a plan view of the top of the cultivation bottle in which the surface of a culture medium was inoculated with a liquid seed culture. In FIG. 1, A is the liquid seed culture inoculated portion and B and C are liquid seed culture non-inoculated portions. The cap was then removed and the cultivation bottle was reversed. Thereafter, the bottle was transferred to a sprouting room where the temperature was controlled to 15° C. and the humidity was controlled to 115 to 120% as the indication value on HUMID EYE 100 (manufactured by Saginomiya Seisakusho, Inc.), and sprouting was carried out for 10 days under the illumination of 5 to 30 lux for growing the primordia to sprouts (budlet). Thereafter, 80 bottles per lot were drawn at random and the number of sprouts (budlet) grown from the primordia on the surface of the culture medium was counted and the average thereof was calculated. Similar measurements were carried out with respect to 10 lots. The results are shown in Table 1.

TABLE 1

| Lot No. | Average number of sprouts (budlet) per cultivation bottle |
| --- | --- |
| 070815 | 85 |
| 070816 | 74 |
| 070817 | 113 |
| 070820 | 95 |

TABLE 1-continued

| Lot No. | Average number of sprouts (budlet) per cultivation bottle |
| --- | --- |
| 070821 | 58 |
| 070822 | 78 |
| 070823 | 60 |
| 070824 | 125 |
| 070827 | 89 |
| 070828 | 71 |
| Average | 85 |
| Standard deviation | 21.7 |

As shown in Table 1, it was confirmed that a lot of sprouts were formed on the surface of a culture medium. Further, the sprouts were formed throughout the surface of a culture medium.

Comparative Example 1

According to the same manner as that in Example 1, incubation and sprouting were carried out except that 25 mL of the liquid seed culture (dry weight of the mycelia: about 4 g/L) was inoculated on the entire surface of a culture medium. Thereafter, 80 bottles per lot were drawn at random. The number of sprouts (budlet) grown from primordia on the surface of the culture medium was counted and the average thereof was calculated. Similar measurements were carried out with respect to 10 lots. The results are shown in Table 2.

TABLE 2

| Lot No. | Average number of sprouts (budlet) per cultivation bottle |
| --- | --- |
| 070727 | 28 |
| 070730 | 22 |
| 070731 | 19 |
| 070801 | 35 |
| 070802 | 15 |
| 070803 | 26 |
| 070806 | 13 |
| 070807 | 18 |
| 070808 | 15 |
| 070809 | 25 |
| Average | 22 |
| Standard deviation | 6.58 |

As seen from Table 2, the number of sprouts produced in the surface of a culture medium was smaller as compared with Example 1.

Example 2

To a center portion of the surface of a culture medium prepared according to the same method as that of Example 1 filled in each of 12 cultivation bottles per one test group (center portion of the bottle mouth diameter), 25 mL of a liquid seed culture (dry weight of the mycelia: 4.4 g/L) prepared according to the same method as that of Example 1 was inoculated in a circular shape so that a ratio of a liquid seed culture inoculated portion and a liquid seed culture non-inoculated portion was 1:15, 4:12, 8:8, 4:1, or 4:0. Thereafter, incubation and sprouting were carried out under the same conditions as those in Example 1. After sprouting, sprouts other than sprouts in the center of the surface of a culture medium were removed and the bottle was returned to the original position. Thereafter, the culture was transferred to a growth room controlled to a temperature of 15° C. and a humidity of 105 to 120% as the indicated value of a HUMID EYE 100 (Saginomiya Seisakusho, Inc.), illuminated under 50 to 100 lux and grown for 10 days to grow the sprouts into mature fruit body. In each test group, the number of cultivation bottles having established strains of mature fruit body formed by growing of sprouts at the center of the surface of a culture medium is shown in Table 3.

TABLE 3

| Test group | Number of cultivation bottles forming established strain of mature fruit bodies (per 12 cultivation bottles) |
| --- | --- |
| 1:15 | 10 |
| 4:12 | 12 |
| 8:8 | 12 |
| 4:1 | 11 |
| 4:0 | 5 |

As shown in Table 3, in all the test groups whose ratios of liquid seed culture inoculated portions to liquid seed culture non-inoculated portions were 1:15 to 4:1, sufficient numbers of sprouts were formed at the center of the surface of a culture medium and good established strains of mature fruit body could be obtained. In particular, the formation of good established strains of mature fruit body was significant in test groups of the ratios of 4:12 to 8:8. On the other hand, in the test group (4:0) having no liquid seed culture non-inoculated portion (the entire surface of a culture medium was inoculated with the liquid seed culture), in particular, the sprout formation at the center of the surface of a culture medium was considerably inferior to the other test groups. As a result, a sufficient amount of an established strain of fruit body could not be obtained.

Example 3

A diluted solution of a liquid seed culture was prepared by diluting a liquid seed culture (dry weight of the mycelia: 4.4 g/L) prepared according to the same method as that of Example 1 either twice (dry weight of the mycelia 2.2 g/L) or four times (dry weight of the mycelia: 1.1 g/L) with PGY liquid culture medium. To a center portion of the surface of a culture medium prepared according to the same method as that of Example 1 filled in each of 12 cultivation bottles per, 50 mL, 25 mL or 12.5 mL of the above original liquid seed culture, or 12.5 mL of the twice diluted liquid seed culture or 12.5 mL of the four times diluted liquid seed culture were inoculated in a circular pattern so that a ratio of a liquid seed culture inoculated portion and a liquid seed culture non-inoculated portion was 8:8. Thereafter, incubation and sprouting were carried out under the same conditions as those of Example 1. After sprouting, sprouts other than sprouts at the center of the surface of a culture medium were removed and the bottle was returned to the original position. Thereafter, the culture was transferred to a growth room controlled to a temperature of 15° C. and a humidity of 105 to 120% as the indicated value of a HUMID EYE 100 (Saginomiya Seisakusho, Inc.), illuminated under 50 to 100 lux and grown for 10 days to grow the sprouts into mature fruit body. The number of cultivation bottles having established strains of mature fruit body formed by growing of the sprouts at the center of the surface of a culture medium is shown in Table 4.

TABLE 4

| Test group | Weight of mycelia (mg/cm²) | Number of cultivation bottles forming established strain of mature fruit bodies (per 12 cultivation bottles) |
| --- | --- | --- |
| Original liquid 50 ml | 8.8 | 8 |
| Original liquid 25 ml | 4.4 | 11 |
| Original liquid 12.5 ml | 2.2 | 12 |
| Liquid diluted twice 12.5 ml | 1.1 | 12 |
| Liquid diluted four times 12.5 ml | 0.55 | 10 |

As shown in Table 4, formation of sprouts at the center of the surface of a culture medium was good and resulted in good and stable formation of established strains of fruit body in the original liquid 12.5 mL (2.2 mg/cm²) and the twice diluted liquid 12.5 mL (1.1 mg/cm²) sections. For higher or lower weights of the mycelia, stable formation of sprouts at the center of the surface of a culture medium became difficult and the number of established strains of fruit body decreased.

Example 4

Sprouting was carried out according to the same method as that in Example 1. After sprouting, the bottle was returned to the original position. At each of the hole at the center portion of the culture medium and the four holes made at equal intervals on the circumference of the circle of 4 cm diameter at the center part, sprouts other than 2 or 3 sprouts growing from the side surface towards the aperture were removed using a spatula. Thereafter, the culture was transferred to a growth room controlled to a temperature of 15° C. and a humidity of 105 to 120% as the indicated value of a HUMID EYE 100 (Saginomiya Seisakusho, Inc.). By incubating at the illumination of 50 to 100 lux for 10 days, the sprouts were grown into mature fruit body. During that time, growing was carried out by removing unnecessary sprouts so that a single fruit body could be grown from the aperture of the hole. As a result, large hon-shimeji fruit body with about 20 to 30 g per a single stem could be obtained from the center holes.

Example 5

Sprouting was carried out according to the same method as that in Example 1. After sprouting, the resulting sprouts (budlet) were removed. Cuttings with a length of 5 to 20 mm were selected from the removed budlet. Cuttings were transplanted one by one to respective four holes made at equal intervals on the circumference of a circle of 4 cm diameter at the center of the solid culture medium from which the cuttings had been selected and the remaining primordia and budlet had been removed. Thereafter, the culture was transferred to a growth room controlled to a temperature of 15° C. and a humidity of 105 to 120% as the indicated value of a HUMID EYE 100 (Saginomiya Seisakusho, Inc.). By incubating at the illumination of 50 to 100 lux for 10 days, the sprouts were grown into mature fruit body. As a result, large hon-shimeji fruit body could be obtained in a yield of about 70 to 90 g per bottle.

As shown in Table 1 and Table 2, the present invention can provide a hon-shimeji mushroom culture wherein sprouts (budlet) whose number is about 4 times as much as that of a conventional culture are formed on the surface of a culture medium. Furthermore, an established strain of hon-shimeji mushroom fruit body can be stably obtained by taking into account the surface area ratio of the liquid seed culture inoculated portion and the liquid seed culture non-inoculated portion as shown in Table 3 and the weight of strain as shown in Table 4.

Industrial Applicability

According to the present invention, there is provided a fungal bed culture of a hon-shimeji mushroom which enables stable production of a hon-shimeji mushroom by cultivation in a commercially large scale, and a fungal bed cultivation method of a hon-shimeji mushroom using the fungal bed culture. By using the fungal bed culture in the cultivation of a hon-shimeji mushroom, it is possible to achieve a high formation rate of sprouts (budlet) and stable hon-shimeji mushroom cultivation.

BRIEF DESCRIPTION OF THE DRAWINGS

FIG. 1 is a schematic plan view of the top of a culture medium for cultivation (culture medium) illustrating an example of the relationship between a liquid seed culture inoculated portion and a non-inoculated portion on the surface of a culture medium, wherein A is the liquid seed culture inoculated portion and B and C are liquid seed culture non-inoculated portions in a circular doughnut-like shape.

The invention claimed is:

1. A fungal bed culture for bottle cultivation of a hon-shimeji mushroom, comprising a solid culture medium for cultivation inoculated with a liquid seed culture of a hon-shimeji mushroom, wherein the surface of said solid culture medium for cultivation has a liquid seed culture inoculated portion and a liquid seed culture non-inoculated portion, and wherein the liquid seed culture inoculated portion has a circle, oval, circular doughnut-like or oval doughnut-like shape plan view.

2. The fungal bed culture of a hon-shimeji mushroom according to claim 1, wherein the liquid seed culture is inoculated in an amount of 0.05 to 5 mL/cm² at the liquid seed culture inoculated portion.

3. A fungal bed cultivation method of a hon-shimeji mushroom, comprising incubating the fungal bed culture of a hon-shimeji mushroom according to claim 1 to generate a fruit body from the fungal bed culture.

* * * * *